United States Patent
Struble

[11] Patent Number: 5,871,531
[45] Date of Patent: Feb. 16, 1999

[54] MEDICAL ELECTRICAL LEAD HAVING TAPERED SPIRAL FIXATION

[75] Inventor: Chester Struble, Eijsden, Netherlands

[73] Assignee: Medtronic, Inc., Minneapolis, Minn.

[21] Appl. No.: 936,992

[22] Filed: Sep. 25, 1997

[51] Int. Cl.⁶ .................................................. A61N 1/05
[52] U.S. Cl. ........................ 607/126; 607/116; 607/122; 600/375; 600/377
[58] Field of Search ............................ 607/115–119, 122, 607/123, 124, 126, 127, 129–131, 133–138, 147, 149; 600/372–381, 393

[56] References Cited

U.S. PATENT DOCUMENTS

| | | | |
|---|---|---|---|
| 4,922,927 | 5/1990 | Fine et al. | 607/122 |
| 5,076,285 | 12/1991 | Hess et al. | 607/127 |
| 5,300,108 | 4/1994 | Rebell et al. | 607/127 |
| 5,423,865 | 6/1995 | Bowald et al. | 607/126 |
| 5,643,255 | 7/1997 | Organ | 607/122 |

*Primary Examiner*—William E. Kamm
*Assistant Examiner*—Kennedy J. Schaetzle
*Attorney, Agent, or Firm*—Michael J. Jaro; Harold Patton

[57] ABSTRACT

A transvenous lead specifically designed for coronary sinus implantation. The lead of the present invention features an electrode/anchoring portion at its distal end. The electrode/anchoring portion features a dual tapered self-propelling spiral electrode. Through this design the electrode supplies excellent direct electrical contact to the inside of the vessel. The dual tapered spiral permits the electrode to either be propelled forward within the vessel and toward the more distal locations by turning in a first direction and also permits the electrode to be propelled backwards within the vessel toward the more proximal locations by turning in a second, opposite direction. The spiral shape does not obstruct blood flow. The taper to the spiral also permits the electrode portion to be placed through any valves which may be within the vessel without causing damage. Through this design the lead provides the ability to electrically sense and stimulate many areas along the coronary sinus and its related vessels such that either the left atrium or left ventricle of the heart may be electrically stimulated.

22 Claims, 5 Drawing Sheets

MEDICAL ELECTRICAL LEAD HAVING TAPERED SPIRAL FIXATION

FIELD OF THE INVENTION

This invention relates to the field of body implantable medical device systems, and in particular to a body implantable medical device system which includes a medical electrical lead particularly designed for implantation into the coronary sinus.

BACKGROUND OF THE INVENTION

Modern electrical therapeutic and diagnostic devices for the heart, such as pacemakers, cardiovertors, and defibrillators, for example, require a reliable electrical connection between the device and a region of the heart. Typically, a medical electrical "lead" is used for the desired electrical connection.

One type of commonly used implantable lead is a transvenous lead. Transvenous leads are positioned through the venous system to attach or electrically connect at their distal end to the heart. At their proximal end, they are connected to typically an implantable pulse generator. Such leads normally took the form of a long, generally straight, flexible, insulated conductor. Among the many advantages of a transvenous lead is that it permits an electrical contact with the heart without physically exposing the heart itself, i.e., major thoracic surgery is not required.

The specific design of a transvenous lead used is often varied depending upon the region of the heart to which it is to be connected. For example, U.S. Pat. No. 4,402,330 of Lindemans discloses a body implantable lead in which the lead body has a J-curve and the distal electrode has a permanent bend. In such a manner, the lead is configured to electrically connect to the right atrium.

While such a lead has been found acceptable for electrically connecting and thus pacing the right atrium, the need exists for a transvenous medical electrical lead which may provide an electrical connection to the left atrium or even the left ventricle. Of course the left side of the heart cannot, at present, be transvenously accessed with a lead for chronic implantation due to the direction of blood flow and the present limitations of materials. To be precise, blood flows through the right side of the heart (atrium and ventricle), through the lungs, through the left side of the heart (atrium and ventricle) and then through the rest of the body, including the brain, before returning again to the right side of the heart. Implanted objects, however, may cause minor blood clots and thrombus to form in the blood. These may, on occasion, dislodge and be released into the bloodstream. Because the blood circulates directly from the left atrium and ventricle to the brain, any clots, however minor, could have serious consequences if they were to reach the brain, e.g. a stroke. In contrast, any clots released from an object implanted in the right side of the heart would simply travel to the lungs, where they would lodge without any serious risk. Thus at present, chronic transvenous leads may not be safely implanted within the left side of the heart.

In spite of the difficulties, there remains a great need to be able to electrically stimulate or sense or both the left side of the heart. The most obvious reason is the left side of the heart accounts for the majority of the heart's hemodynamic output. For example, the left ventricle has a greater wall thickness (10–20 mm as compared to 1–5 mm) than the right side. This, of course, is reasonable given that the left side of the heart must pump blood throughout the body while the right side only pumps blood through the lungs.

Because the left side is relatively more important for hemodynamic output, not surprisingly, various pathologies may be better treated through stimulation on the left side of the heart. For example, in patients with dilated cardiomyopathy, electrical stimulation of both the right side and the left side of the heart has been shown to be of major importance to improve the patient's well-being and manage heart failure. See, for example, Cazeau et al., "Four Chamber Pacing in Dilated Cardiomyopathy," PACE, November 1994, pgs. 1974–79. See also Brecker and Fontainem,St. et al., "Effects Of Dual Chamber Pacing With Short Atrioventricular Delay In Dilated Cardiomyopathy," Lancet November 1992 Vol. 340 p1308–1312; Xiao H. B. et al., "Effect Of Left Bundle Branch Block On Diastolic Function In Dilated Cardiomyopathy," Br. Heart J 1991, 66(6) p 443–447; and Fontaine G et al, "Electrophysiology Of Pseudofunction," CI.Meere (ed.) Cardiac pacing, state of the art 1979, Pacesymp, 1979 Montreal..

At present there are several techniques for implanting a lead onto or into the left side of the heart. First, of course, is through general thoracic surgery; either via a median sternotomy; intercostal approach; or, in a more limited procedure, a sub-xiphoid approach. These procedures, however, involve major surgery which may be painful and dangerous for the patient, as well as extremely costly. The sub-xiphoid approach, moreover, only permits limited access. Another approach used to electrically access the left side of the heart is through the coronary sinus.

The coronary sinus, however, presents challenges in both implanting the lead in the proper position as well as ensuring the lead maintains sufficient electrical contact with the desired tissue. For example, coronary sinus and the related vessels are vital to the proper circulating of blood through the heart tissue. Thus, the occlusion of blood flow in the vessel by a lead should not occur. Moreover, the lead should not cause, by its presence, an extensive amount of thrombosis to form. Both the occlusion and thrombosis may hinder blood flow to the point that stagnation occurs in the vessel. The health of the surrounding tissue would be impacted. Moreover, the coronary sinus and its related vessels typically have an extremely tortuous path, especially in the more distal locations. These locations, however, are the preferred locations for providing electrical stimulation. Thus such leads must be able to follow and remain within the various tortuous locations within the coronary sinus and its related vessels. Once the lead is properly positioned it is essential that the electrode has good contact with the inside of the vessel. Further complicating matters is the fact that blood valves may be present within various portions of the coronary sinus and its related vessels. These valves may hinder the passage of the lead through the vessel. Due to the many obstacles faced by placing a lead within these vessels, it is thus preferred by physicians that the lead be able to be placed using a guide wire.

It is thus an object of the present invention to provide a medical electrical lead which may be positioned within the more distal tortuous portions of the coronary sinus and its related vessels.

A further object of the present invention is to provide such a lead which will not occlude blood flow through the vessel in which it is placed.

It is a further object of the present invention to provide a lead having an electrode which will maintain good contact with the inside of the vessel wall and thereby provide excellent electrical properties.

It is a still further object of the present invention is to provide a medical electrical lead which may be positioned along a selected portion of the coronary sinus wall placed using a guide wire.

It is a still further object of the present invention is to provide a medical electrical lead having an electrode which may be easily positioned along a selected portion of the coronary sinus wall through rotation of the electrode portion, but which may be as easily removed from the coronary sinus through counter rotation of the electrode portion.

SUMMARY OF THE INVENTION

These and other objects are accomplished through the present invention. In one embodiment, the present invention comprises a transvenous lead specifically designed for coronary sinus implantation. The lead of the present invention features an electrode/anchoring portion at its distal end. The electrode/anchoring portion features a dual tapered self-propelling spiral electrode. Through this design the electrode supplies excellent direct electrical contact to the inside of the vessel. The dual tapered spiral permits the electrode to either be propelled forward within the vessel and toward the more distal locations by turning in a first direction and also permits the electrode to be propelled backwards within the vessel toward the more proximal locations by turning in a second, opposite direction. The spiral shape does not obstruct blood flow. The taper to the spiral also permits the electrode portion to be positioned through any valves which may be within the vessel without causing damage. Through this design the lead provides the ability to electrically sense and stimulate many areas along the coronary sinus and its related vessels such that either the left atrium or left ventricle of the heart may be electrically stimulated.

BRIEF DESCRIPTION OF THE FIGS.

It should be understood the FIGS. are not necessarily to scale.

DETAILED DESCRIPTION OF THE INVENTION

Figure 1:
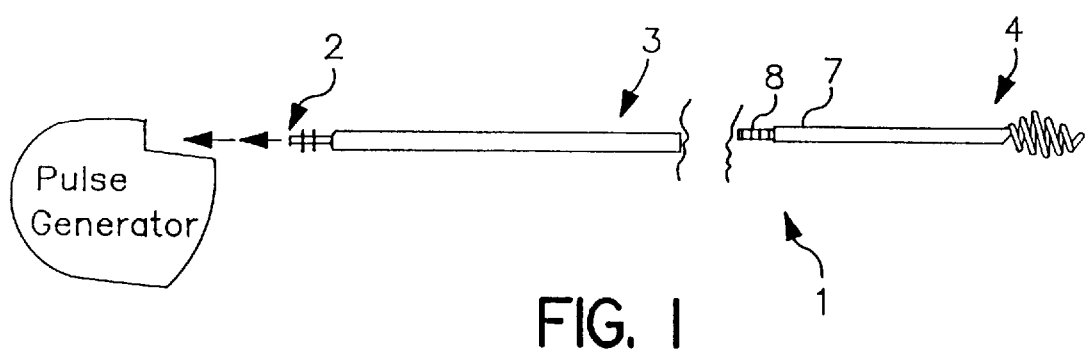
FIG. 1 is a view of an implantable electrical stimulation system which features a lead according to the present invention.

FIG. 1 is a view of an implantable electrical stimulation system which features a lead according to the present invention. The implantable electrical stimulation system features a pulse generator into which a lead 1 is coupled. Pulse generator may be of any acceptable design, such as a Kappa™ DDDR pacemaker available from Medtronic Inc., Minneapolis, Minn. Of course, a Kappa™ DDDR pacemaker provides dual chamber therapy and typically a second lead would also be used. Only a single lead 1, however, is shown in this view for purposes of clarity.

As seen, lead 1 essentially has three portions: a connector portion 2, a lead body portion 3 and electrode/anchoring portion 4. Connector portion is a standard pacing connector, such as an IS-1 or an IS BI-2, and is used to couple the lead to a pulse generator, as shown. Of course, other connector designs may be used. Lead body portion 3 is preferably constructed using a insulative sheath 7 of a biocompatible polymer, such as silicone, and a coiled conductor 8 of a biocompatible material, such as MP35N. Of course other materials and structures may also be used for each of these components, such as a BSW conductor, and still be within the scope of the present invention. Lead body portion couples connector portion 2 to electrode/anchoring portion 4.

Figure 2:
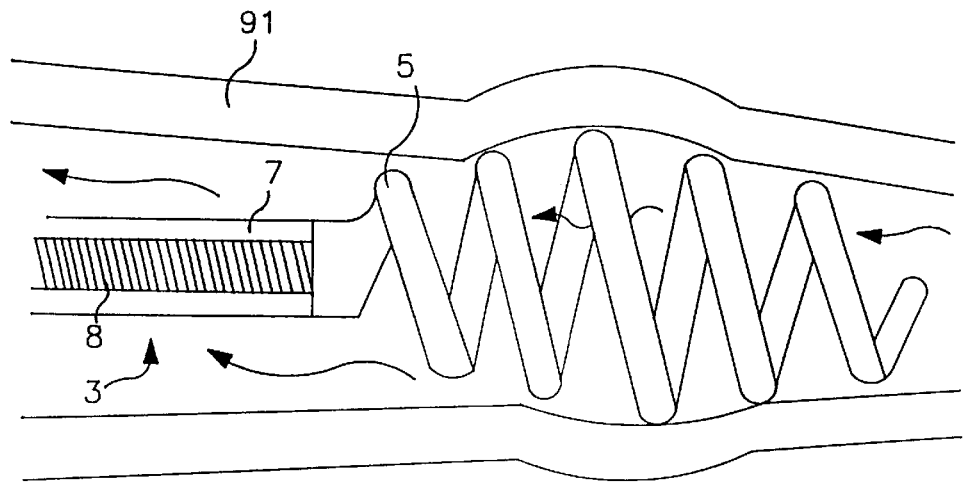
FIG. 2 depicts the distal end of the lead shown in FIG. 1

FIG. 2 depicts the distal end of the lead shown in FIG. 1. As seen, electrode/anchoring portion 4 features a dual tapered self-propelling spiral electrode 5. Spiral electrode comprises a helix having a barrel-shape or dual taper such that the helix has its largest diameter in the middle portion and tapers down to smaller diameters at either end. Through this design the electrode contacts the vessel wall 91 and will thus propel itself into and down along the vessel by rotating in a first direction but will also or propel itself out of and out from the vessel by rotating in a second, opposite direction. The open design of the spiral electrode further provides unobstructed blood flow within the vessel. Electrode 5 is fashioned of a conductive biocompatible alloy, preferably platinum-iridium alloy, as is well know in the art.

Figure 3:
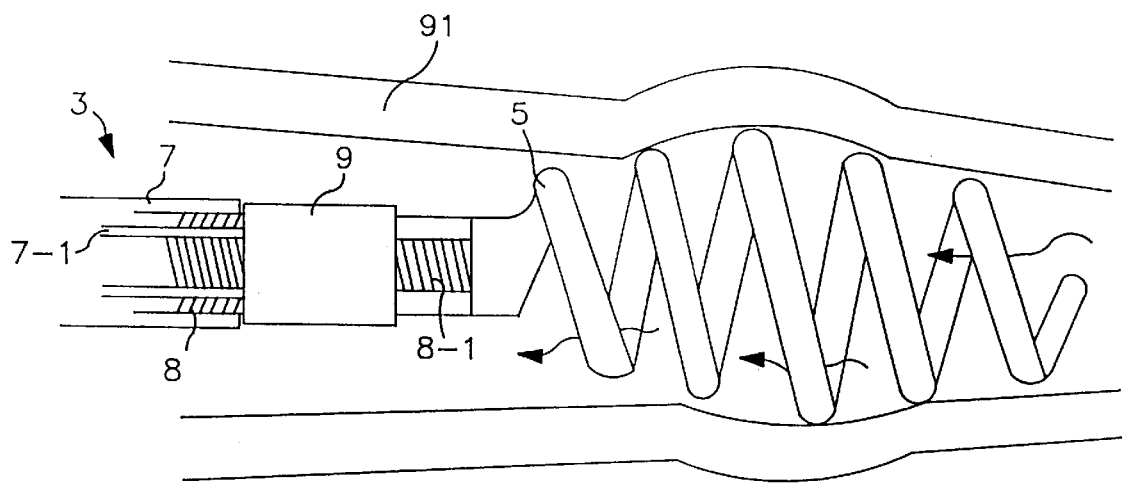
FIG. 3 depicts the distal end of an alternative embodiment of the present invention.
Figure 4:
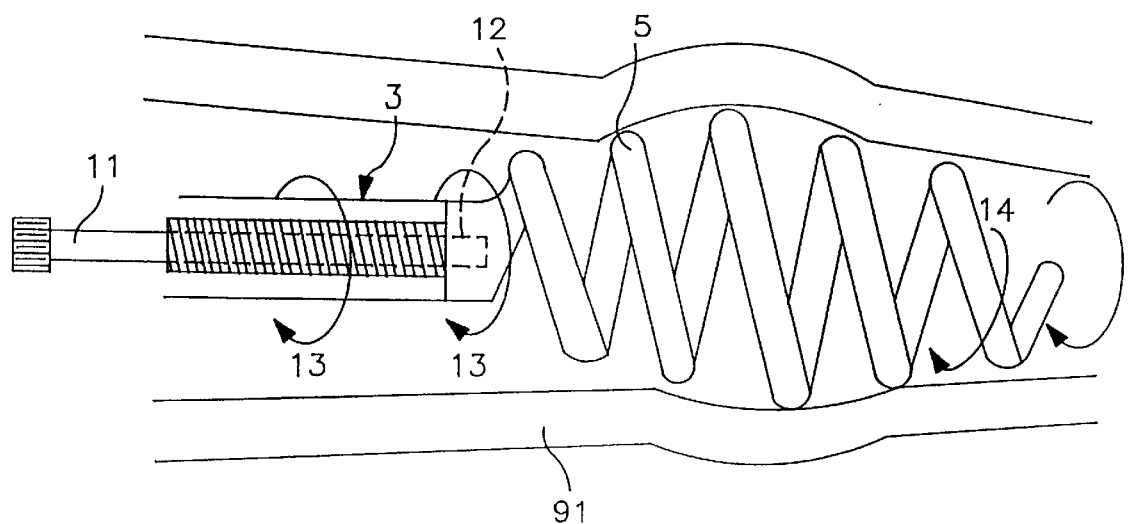
FIG. 4 depicts the distal end of an alternative embodiment of the present invention.

FIG. 3 depicts an alternative embodiment of the present invention. In this embodiment the lead 1 is fashioned for bipolar electrical stimulation or sensing or both. In particular, this embodiment features a second electrode 9 positioned proximal from spiral electrode 5. As seen in this embodiment lead body 3 features an outer insulative sheath 7 and inner insulative sheath 7-1 of a biocompatible polymer, such as silicone, and an outer coiled conductor 8 and an inner coiled conductor 8-1 of a biocompatible material, such as MP35N. Of course other materials and structures may also be used for each of these components. Ring electrode 9 is also preferably constructed of a polished platinum-iridium alloy FIG. 4 depicts an alternative embodiment of the present invention. As discussed above, electrode 5 may be propelled along the vessel by rotation. As seen, the lead 1 is fashioned to accept a standard stylet 11. In this design, lead is rotated about a stylet introduced therein. Due to the dual taper of the electrode 5, the electrode may be moved in either direction along the vessel by turning in either respective direction.

Figure 5:
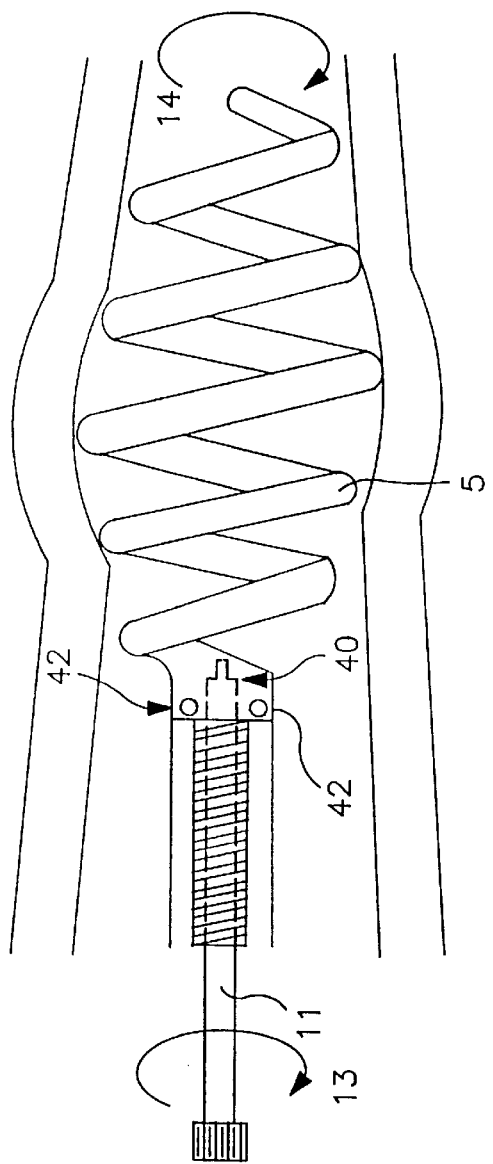
FIG. 5 depicts the distal end of an alternative embodiment of the present invention.

FIG. 5 depicts an alternative embodiment of the present invention. As seen, this embodiment is essentially the same as that depicted in FIG. 2 but for the provision to permit the spiral electrode to rotate independent of the lead body and controlled through a rotational stylet. In particular electrode 5 is mounted to lead body 3 through a series of bearings 42 which permit the electrode to be rotated independently of lead body. As seen electrode 5 interlocks with stylet 11 such that torque may be transferred from the stylet to the spiral electrode and thereby cause the electrode to be rotated independently of lead body.

Figure 6:
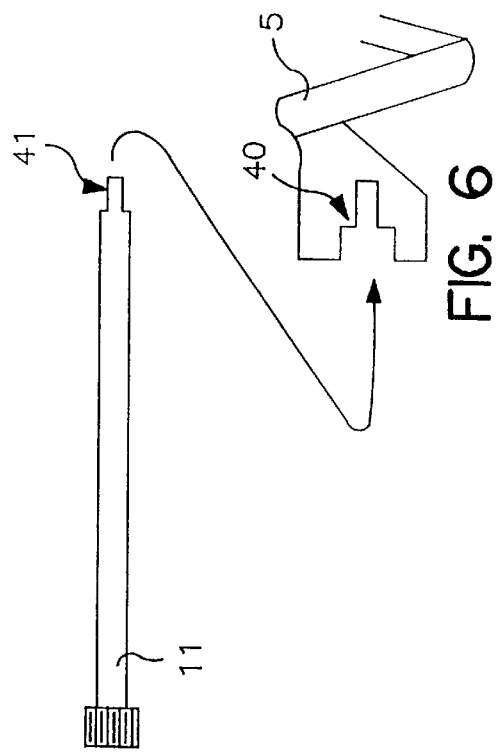
FIG. 6 depicts a detailed view of the interlock between the stylet and spiral electrode depicted in FIG. 5.

FIG. 6 depicts a detailed view of the interlock between the stylet and spiral electrode depicted in FIG. 5. As seen in this embodiment the electrode features a female port 40 into which a correspondingly shaped male member 41 of the stylet can be inserted. Through this design torque may be transferred from the stylet 11 to the electrode 5.

Figure 7:
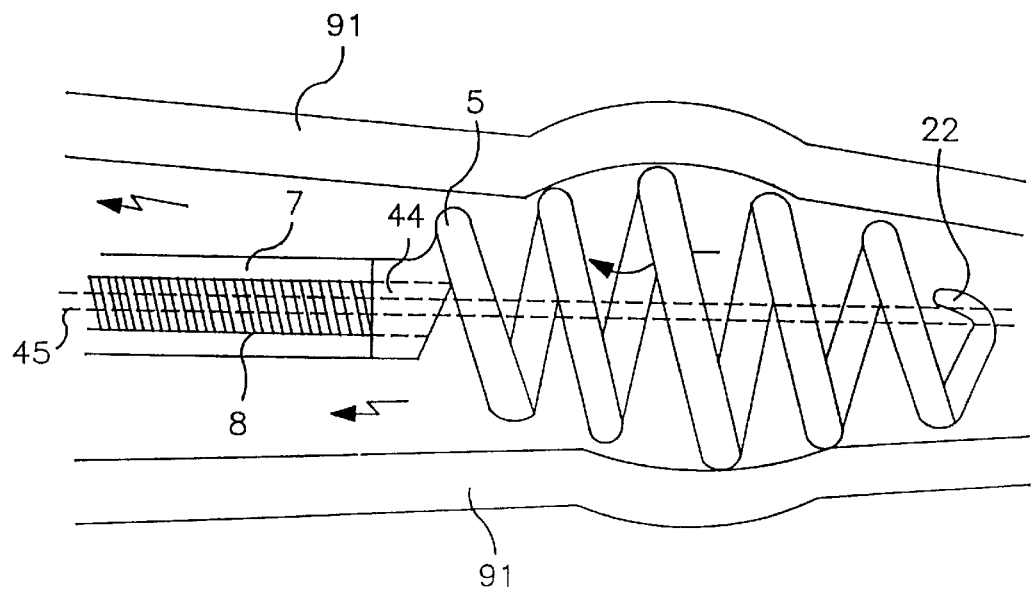
FIG. 7 depicts an alternative embodiment of the present invention.

FIG. 7 depicts an alternative embodiment of the present invention. As seen, this embodiment is essentially the same as that depicted in FIG. 2 but for the provision of an elongated and bent tip 22 at the distal end of spiral electrode 5. Bent tip is provided to decrease the possibility that the tip portion of the spiral electrode will engage within any structures along the vessel wall. This design further features a guide wire lumen 44 which runs through the length of the lead and communicates into the interior of the spiral, thus permitting the lead to be implanted using a guide wire 45 (shown here in phantom) as is well known in the art. All other features of this electrode are the same other than those as disclosed in FIG. 2

Figure 8B:
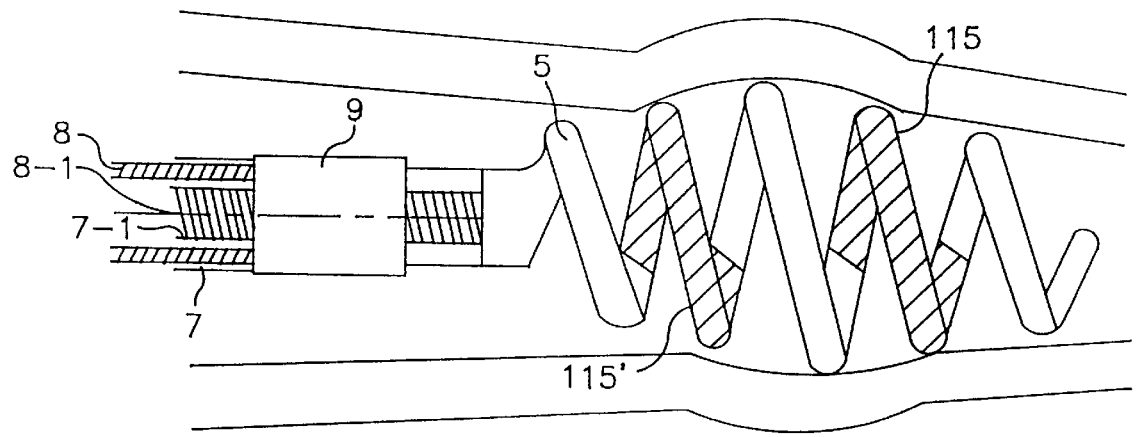
FIG. 8A and 8B depict an alternative embodiments of the present invention.
Figure 8A:
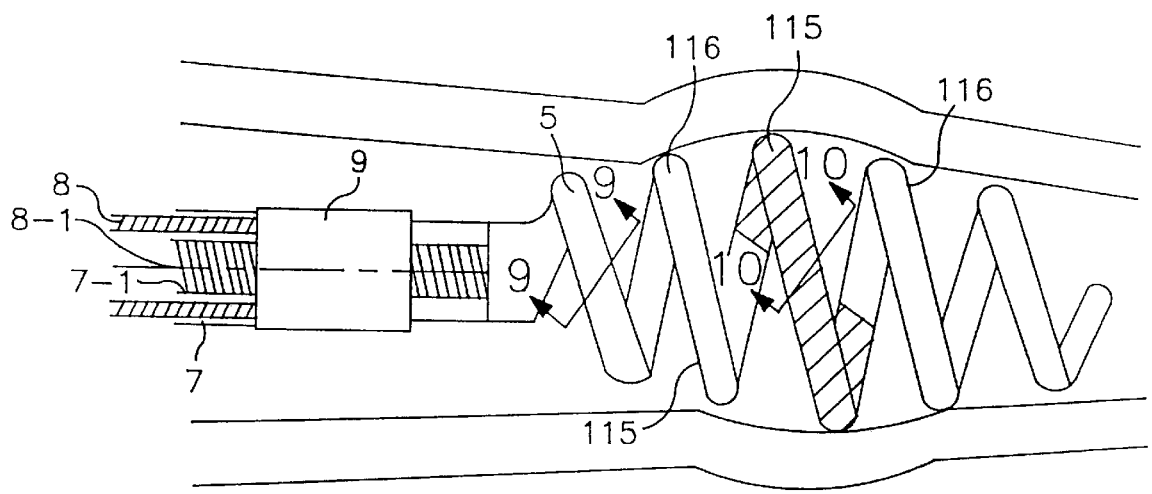

FIG. 8A depicts an alternative embodiment of the present invention. In this embodiment the spiral electrode 5 is constructed such that only the central portion of the spiral has an electrode outer surface. Thus, in this embodiment, only one of the turns 115 of the spiral electrode will electrically contact the vessel wall while the remainder 116 of the spiral on either side is electrically insulated using any of the known biocompatible electrical insulators, such as silicone rubber. In the preferred embodiment the turn which has made electrical contact electrically conductive at its exterior has its central turn spanning its greatest diameter of the spiral electrode. Of course, the particular length of spiral which is conductive may be varied to suit the desired performance of the lead.

FIG. 8B depicts an alternative embodiment of the present invention. This embodiment is similar to that shown in FIG. 8A, but for the turn 115 which is electrically active is positioned on a section of the dual tapered spiral which is not at the largest diameter of the spiral, that is the electrically active portion 115 is not positioned along the central portion of the spiral. has an electrode outer surface. Moreover, although shown as having only one electrically active portion 115, spiral may additionally feature a second electrically active portion, such as that depicted as 115', so as to provide bipolar stimulation and sensing directly against the coronary sinus wall.

Figures 9, 10:
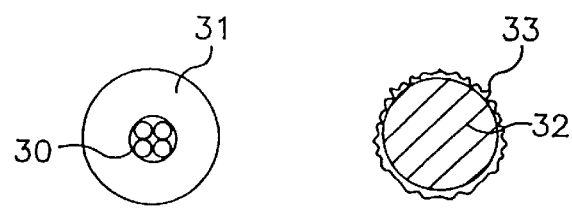
FIG. 9 is a cross-section across the electrode shown in FIG. 8A along the line 9—9.
FIG. 10 is a cross-sectional view of the electrode shown in FIG. 8B taken along the line 10—10.

FIG. 9 is a cross-section across the electrode shown in FIG. 8A along the line 9—9. As seen, in this portion of spiral electrode the outer surface is not electrically conductive and is constructed having a central core of a conductive material 30 surrounded by an outer insulative material 31. Conductive core is preferably a biocompatible alloy such as MP35N and insulative material is preferably a biocompatible polymer such as silicone. Of course, other materials may also be selected and be within the scope of the present invention. One important feature of this construction as compared to that used in FIG. 2, is that through this construction the spiral is made more pliable, as compared to a solid conductor spiral.

FIG. 10 is a cross-sectional view of the electrode shown in FIG. 8A taken along the line 10—10. In this portion of the electrode the outer surface is made electrically conductive. In this embodiment this portion is constructed from a solid core 32 of a electrically conductive material such as MP35N. The exterior surface of this core may also be treated to enhance its electrical properties such as a coating of porous spherical powder which has been further platinized with a deposit of platinum black depicted as structure 33 in this Figure. In addition, electrode may further be constructed having a cavity into which is disposed a monolithic controlled release device therein to elute or dispense a drug, such as the sodium salt of dexamethasone, from the electrode into the surrounding tissues, as is well known in the pacing art. In an alternative, the electrode may be treated with a very slightly soluble in water steroid, such as beclomethasone dipropionate anhydrous.

Preferably the steroid is applied to the surface of the electrode which contacts tissue when implanted. Further details of such a coating process may be found in the copending U.S. Patent Application of Williams "Medical Electrical Lead" Ser. No. 08/605,591, incorporated herein by reference.

It is to be understood that the present invention is not limited to use only in pacing leads, and may be employed in the construction of may of various type of therapeutic and diagnostic devices, including defibrillation leads, intended to be disposed within the coronary sinus. In fact, for the purposes of this specification and claims, the term "lead" is used herein in its broadest sense and includes any stimulation lead or sensing lead, a combination thereof or any other elongated member, such as a catheter, which may usefully be introduced into a body. For purposes of illustration only, however, the present invention has been described in the context of transvenous pacing lead. In addition, although the term "coronary sinus" has been used, this is for purposes of illustration only and it should be understood the present invention is useful in positioning a lead along any portion of the vascular system, including the great cardiac vein, or any of the other numerous veins or even arteries within the body into which a lead may be implanted.

Although a specific embodiment of the invention has been disclosed, this is done for purposes of illustration and is not intended to be limiting with regard to the scope of the invention. It is contemplated various substitutions, alterations and/or modifications may be made to the disclosed embodiment without departing from the spirit and scope of the invention. Such modifications may include substituting elements or components which perform substantially the same function in substantially the same way to achieve substantially the same result for those described herein.

What is claimed is:

1. A medical electrical lead comprising
    means for electrically coupling to a pulse generator
    a lead body coupled to the means for electrically coupling, the lead body having a first lead body end and a second lead body end, the lead body further having a conductor having a first conductor end and a second conductor end and an insulator covering the conductor between the first conductor end and the second conductor end,
    tapered spiral means for maintaining contact with a blood vessel wall, the tapered spiral means coupled to the first end of the lead body, the tapered spiral means having a first spiral end diameter, a middle spiral diameter and a second spiral end diameter, the middle spiral diameter greater than the first spiral end diameter and the second spiral end diameter; and
    an electrode coupled to the second conductor end.

2. A medical electrical lead according to claim 1 wherein the electrode is positioned on the tapered spiral means.

3. A medical electrical lead according to claim 1 means for rotatably coupling the tapered spiral means to the first end of the lead body.

4. A medical electrical lead according to claim 1 wherein the tapered spiral means comprises a length of a biocompatible conductor.

5. A medical electrical lead according to claim 4 wherein the electrode is positioned on the tapered spiral means at a position having the second spiral end diameter.

6. A medical electrical lead according to claim 4 wherein the length of a biocompatible conductor is covered by an insulator.

7. A medical electrical lead according to claim 4 wherein the tapered spiral means comprises a spiral having a taper in a first direction and an opposite taper in a second direction.

8. A medical electrical lead according to claim 1 wherein the tapered spiral means comprises a conductor covered by an insulator, said electrode positioned on the spiral and electrically coupled to the conductor.

9. A medical electrical lead according to claim 8 wherein the tapered spiral means has a first spiral end diameter, a middle spiral diameter and a second spiral end diameter, the middle spiral diameter greater than the first spiral end diameter and the second spiral end diameter.

10. A medical electrical lead according to claim 9 wherein the electrode is positioned on the tapered spiral means at a position having the first spiral diameter.

11. A medical electrical lead according to claim 1 wherein the tapered spiral means is coupled to the first end of the lead body by at least one bearing whereby the tapered spiral means may be independently rotated with respect to the lead body.

12. A medical electrical lead comprising means for electrically coupling to a pulse generator, the means for electrically coupling having an axial lumen a lead body coupled to the means for electrically coupling, the lead body having a first lead body end and a second lead body end, the lead body further having a conductor having a first conductor end and a second conductor end and an insulator covering the conductor between the first conductor end and the second conductor end, the lead body having a lead body lumen, the lead body lumen communicating with the axial lumen of the means for electrically coupling;

tapered spiral means for maintaining contact with a blood vessel wall, the tapered spiral means coupled to the first end of the lead body, the tapered spiral means defining a tapered volume therein, the lead body lumen communicating with the tapered volume;

an electrode coupled to the second conductor end; and a guide wire, positioned within the axial lumen, the lead body lumen and extending within the tapered volume.

13. A medical electrical lead according to claim 12 wherein the electrode is positioned on the tapered spiral means.

14. A medical electrical lead according to claim 12 means for rotatably coupling the tapered spiral means to the first end of the lead body.

15. A medical electrical lead according to claim 12 wherein tapered spiral means comprises a length of a biocompatible conductor, the tapered spiral means having a first spiral end diameter, a middle spiral diameter and a second spiral end diameter, the middle spiral diameter greater than the first spiral end diameter and the second spiral end diameter.

16. A medical electrical lead according to claim 15 wherein the electrode is positioned on the tapered spiral means at a position having the second spiral end diameter.

17. A medical electrical lead according to claim 16 wherein the length of a biocompatible conductor is covered by an insulator.

18. A medical electrical lead according to claim 16 wherein the tapered spiral means comprises a spiral having a taper in a first direction and an opposite taper in a second direction.

19. A medical electrical lead according to claim 12 wherein the tapered spiral means comprises a conductor covered by an insulator, said electrode positioned on the spiral and electrically coupled to the conductor.

20. A medical electrical lead according to claim 19 wherein the tapered spiral means has a first spiral end diameter, a middle spiral diameter and a second spiral end diameter, the middle spiral diameter greater than the first spiral end diameter and the second spiral end diameter.

21. A medical electrical lead according to claim 20 wherein the electrode is positioned on the tapered spiral means at a position having the first spiral diameter.

22. A medical electrical lead according to claim 20 wherein the electrode is positioned on the tapered spiral means at a position having a diameter less than the middle spiral diameter.

* * * * *